(12) United States Patent
Scott (10) Patent No.: US 12,343,245 B2
(45) Date of Patent: Jul. 1, 2025

(54) URINE COLLECTION SYSTEMS, AND METHODS OF MAKING AND USING THE SAME

(71) Applicant: James William Scott, Crawfordville, FL (US)

(72) Inventor: James William Scott, Crawfordville, FL (US)

(*) Notice: Subject to any disclaimer, the term of this patent is extended or adjusted under 35 U.S.C. 154(b) by 198 days.

(21) Appl. No.: 17/868,092

(22) Filed: Jul. 19, 2022

(65) Prior Publication Data

US 2024/0024170 A1 Jan. 25, 2024

(51) Int. Cl.
| | |
|---|---|
| *A61F 13/15* | (2006.01) |
| *A61F 13/512* | (2006.01) |
| *A61F 13/513* | (2006.01) |

(52) U.S. Cl.
CPC ............. *A61F 13/5123* (2013.01); *A61F 2013/15146* (2013.01); *A61F 2013/5127* (2013.01); *A61F 2013/51372* (2013.01)

(58) Field of Classification Search
CPC ............. A61F 13/5123; A61F 13/5116; A61F 2013/15146; A61F 13/515; A61F 2013/51372; A61F 13/5127; A61F 5/455; A61F 5/4556; A61G 9/00; A61G 9/003
See application file for complete search history.

(56) References Cited

U.S. PATENT DOCUMENTS

| | | | | |
|---|---|---|---|---|
| 3,929,135 | A * | 12/1975 | Thompson | B32B 3/28 604/374 |
| 4,645,500 | A * | 2/1987 | Steer | A61F 13/5116 604/378 |
| 5,176,667 | A * | 1/1993 | DeBring | A61B 46/00 4/144.1 |
| 5,713,884 | A * | 2/1998 | Osborn, III | A61F 13/532 604/385.24 |
| 6,202,689 | B1 * | 3/2001 | Williams | A61M 1/84 137/561 R |
| 7,102,054 | B1 * | 9/2006 | Cree | A61F 13/53717 604/378 |
| 11,413,206 | B1 * | 8/2022 | Lance | A61B 5/150045 |
| 2003/0124928 | A1 * | 7/2003 | Sherrod | A47C 27/006 442/79 |
| 2015/0313766 | A1 * | 11/2015 | Miao | A61F 13/5125 604/385.101 |

* cited by examiner

*Primary Examiner* — Susan S Su
*Assistant Examiner* — Erin A Kim
(74) *Attorney, Agent, or Firm* — Thomas | Horstemeyer, LLP (57) ABSTRACT

Urine collection systems are disclosed. Methods of making and using urine collection systems are also disclosed.

23 Claims, 9 Drawing Sheets

URINE COLLECTION SYSTEMS, AND METHODS OF MAKING AND USING THE SAME

FIELD OF THE INVENTION

The present invention is directed to urine collection systems. The present invention is further directed to methods of making and using urine collection systems.

BACKGROUND

Urinary catheters pose numerous problems for patients and hospitals including, but not limited to, patient infections. Absorbent pads may be placed underneath a patient to collect urine, but typically, the pads become soaked in urine, causing discomfort for the patient, and a mess for the patient's caregiver and/or hospital.

Efforts continue to further develop urine collection systems that provide one or more advantages over known urine collection systems.

SUMMARY

The present invention addresses some of the difficulties and problems in the art by the discovery of new urine collection systems.

Accordingly, the present invention is directed to urine collection systems. In one exemplary embodiment, the urine collection systems of the present invention comprise: a perforated sheet having a perforated sheet outer periphery, a perforated sheet upper surface, a perforated sheet lower surface, and a plurality of perforated sheet apertures (i) within the perforated sheet outer periphery, and (ii) extending from the perforated sheet upper surface to the perforated sheet lower surface; wherein at least a portion of the perforated sheet apertures within the plurality of perforated sheet apertures comprises a urine backflow feature that allows one-way urine flow through a given perforated sheet aperture, and prevents urine backflow through the given perforated sheet aperture.

In another exemplary embodiment, the urine collection systems of the present invention comprise: (I) a perforated sheet having a perforated sheet outer periphery, a perforated sheet upper surface, a perforated sheet lower surface, and a plurality of perforated sheet apertures (i) within the perforated sheet outer periphery, and (ii) extending from the perforated sheet upper surface to the perforated sheet lower surface; wherein at least a portion of the perforated sheet apertures within the plurality of perforated sheet apertures comprises a urine backflow feature that allows one-way urine flow through a given perforated sheet aperture, and prevents urine backflow through the given perforated sheet aperture; and (II) an absorbent layer positioned below the perforated sheet, the absorbent layer comprising a fiber-containing layer.

In yet another exemplary embodiment, the urine collection systems of the present invention comprise: (I) a perforated sheet having a perforated sheet outer periphery, a perforated sheet upper surface, a perforated sheet lower surface, and a plurality of perforated sheet apertures (i) within the perforated sheet outer periphery, and (ii) extending from the perforated sheet upper surface to the perforated sheet lower surface; wherein at least a portion of the perforated sheet apertures within the plurality of perforated sheet apertures comprises a urine backflow feature that allows one-way urine flow through a given perforated sheet aperture, and prevents urine backflow through the given perforated sheet aperture; and (II) a bottom sheet positioned below the perforated sheet, the bottom sheet having a bottom sheet upper surface, a bottom sheet lower surface, a major surface portion extending within a plane containing the bottom sheet upper surface, and one or more grooves along a bottom sheet outer periphery of the bottom sheet upper surface The present invention further relates to methods of making urine collection systems. In one exemplary embodiment, the method of making an urine collection system comprises: forming a perforated sheet, wherein the perforated sheet has a perforated sheet outer periphery, a perforated sheet upper surface, a perforated sheet lower surface, and a plurality of perforated sheet apertures (i) within the perforated sheet outer periphery, and (ii) extending from the perforated sheet upper surface to the perforated sheet lower surface; wherein at least a portion of the perforated sheet apertures within the plurality of perforated sheet apertures comprises a urine backflow feature that allows one-way urine flow through a given perforated sheet aperture, and prevents urine backflow through the given perforated sheet aperture.

The present invention even further relates to methods of using urine collection systems. In one exemplary embodiment, the method of using a urine collection system comprises a method of collecting urine from a patient, wherein the method comprise: positioning a perforated sheet under the patient, wherein the perforated sheet has a perforated sheet outer periphery, a perforated sheet upper surface, a perforated sheet lower surface, and a plurality of perforated sheet apertures (i) within the perforated sheet outer periphery, and (ii) extending from the perforated sheet upper surface to the perforated sheet lower surface; wherein at least a portion of the perforated sheet apertures within the plurality of perforated sheet apertures comprises a urine backflow feature that allows one-way urine flow through a given perforated sheet aperture, and prevents urine backflow through the given perforated sheet aperture.

These and other features and advantages of the present invention will become apparent after a review of the following detailed description of the disclosed embodiments and the appended claims.

BRIEF DESCRIPTION OF THE FIGURES

The present invention is further described with reference to the appended figures, wherein.

DETAILED DESCRIPTION

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

With continued reference to the drawings, the present invention will be described with respect to several embodiments showing urine collection systems. FIGS. 1-4, and 11-12 show one exemplary urine collection system 100 of the present invention. As shown in FIGS. 1-4, and 11-12, exemplary urine collection system 100 comprises: (I) a perforated sheet 10 having a perforated sheet outer periphery 11, a perforated sheet upper surface 12, a perforated sheet lower surface 13, and a plurality of perforated sheet apertures 14 (i) within the perforated sheet outer periphery 11, and (ii) extending from the perforated sheet upper surface 12 to the perforated sheet lower surface 13, wherein at least a portion of the perforated sheet apertures 14 within the plurality of perforated sheet apertures 14 comprises a urine backflow feature 15 that allows one-way urine flow through a given perforated sheet aperture 14, and prevents urine backflow through the given perforated sheet aperture 14; and (II) a bottom sheet 40 positioned below the perforated sheet 10, the bottom sheet 40 having a bottom sheet upper surface 42, a bottom sheet lower surface 43, a major surface portion 42' extending within a plane P containing the bottom sheet upper surface 42, and one or more grooves 45 along a bottom sheet outer periphery 41 of the bottom sheet upper surface 42, wherein each groove 45 has a groove length $G_L$, a groove width $G_W$, and a groove depth $G_D$ that enables collection of urine along the bottom sheet outer periphery 41 of the bottom sheet upper surface 42.

Figure 10:
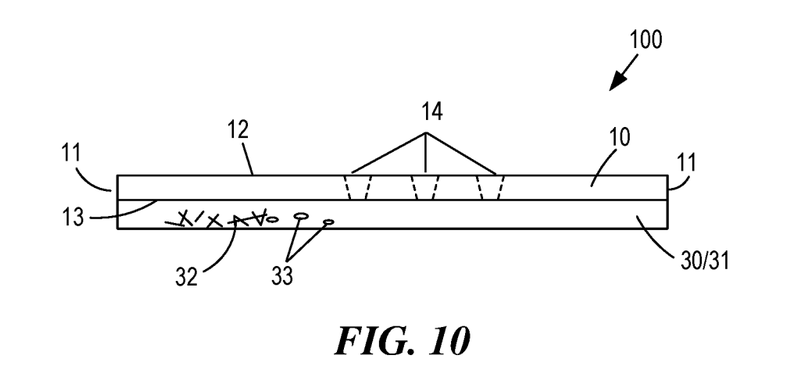
FIG. 10 is a side view of another exemplary urine collection system of the present invention, wherein the exemplary urine collection system comprises a perforated sheet as shown in FIG. 4 in combination with an absorbent layer.
Figure 11:
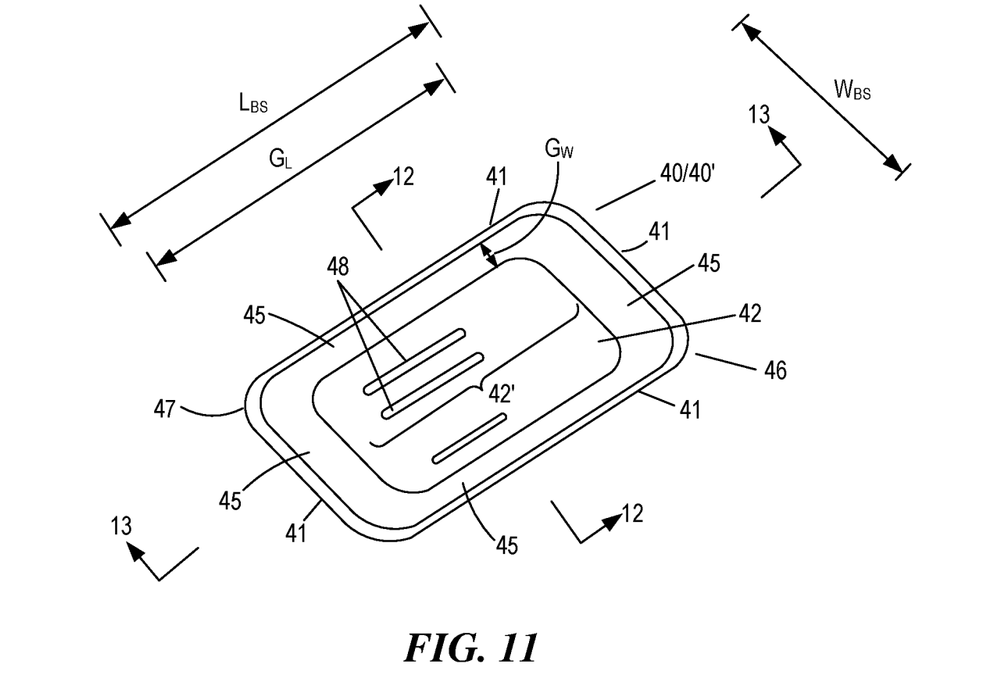
FIG. 11 is a perspective, top view of an exemplary bottom sheet suitable for use in the urine collection systems of the present invention including the exemplary urine collection system shown in FIG. 1.
Figure 12:
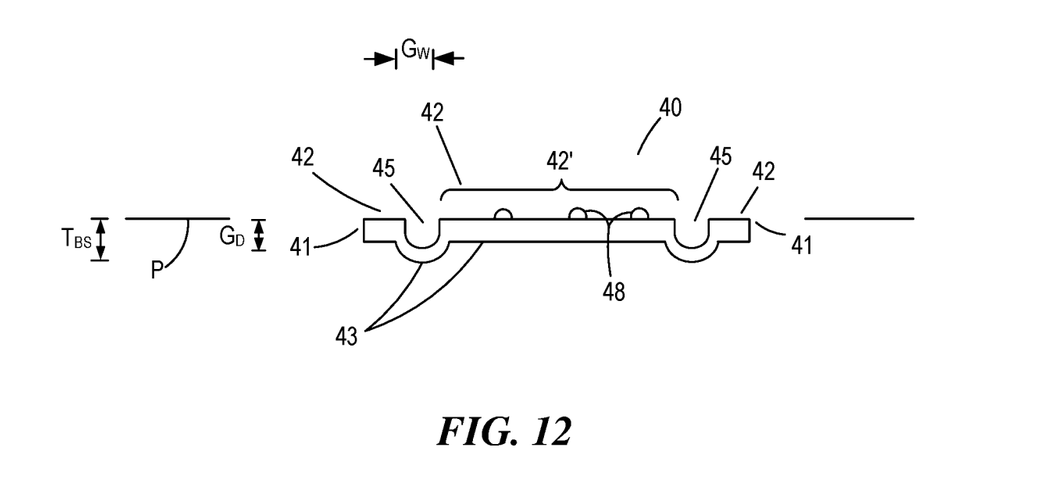
FIG. 12 is a cross-sectional view of the exemplary bottom sheet shown in FIG. 11 as viewed along line 11-11 shown in FIG. 12.

FIG. 10 shows another exemplary urine collection system 100 of the present invention. As shown in FIG. 10, exemplary urine collection system 100 comprises: (I) a perforated sheet 10 having a perforated sheet outer periphery 11, a perforated sheet upper surface 12, a perforated sheet lower surface 13, and a plurality of perforated sheet apertures 14 (i) within the perforated sheet outer periphery 11, and (ii) extending from the perforated sheet upper surface 12 to the perforated sheet lower surface 13, wherein at least a portion of the perforated sheet apertures 14 within the plurality of perforated sheet apertures 14 comprises a urine backflow feature 15 that allows one-way urine flow through a given perforated sheet aperture 14, and prevents urine backflow through the given perforated sheet aperture 14; and (II) an absorbent layer 30 that is positionable below the perforated sheet 10, the absorbent layer 30 comprising a fiber-containing layer 31.

Other exemplary urine collection systems 100 of the present invention comprise: (I) a perforated sheet 10 having a perforated sheet outer periphery 11, a perforated sheet upper surface 12, a perforated sheet lower surface 13, and a plurality of perforated sheet apertures 14 (i) within the perforated sheet outer periphery 11, and (ii) extending from the perforated sheet upper surface 12 to the perforated sheet lower surface 13, wherein at least a portion of the perforated sheet apertures 14 within the plurality of perforated sheet apertures 14 comprises a urine backflow feature 15 that allows one-way urine flow through a given perforated sheet aperture 14, and prevents urine backflow through the given perforated sheet aperture 14; (II) an absorbent layer 30 that is positionable below the perforated sheet 10, the absorbent layer 30 comprising a fiber-containing layer 31; and (III) a bottom sheet 40 positioned below the perforated sheet 10 and the absorbent layer 30, the bottom sheet 40 having a bottom sheet upper surface 42, a bottom sheet lower surface 43, a major surface portion 42' extending within a plane P containing the bottom sheet upper surface 42, and one or more grooves 45 along a bottom sheet outer periphery 41 of the bottom sheet upper surface 42, wherein each groove 45 has a groove length $G_L$, a groove width $G_W$, and a groove depth $G_D$ that enables collection of urine along the bottom sheet outer periphery 41 of the bottom sheet upper surface 42.

The (I) urine collection systems 10, (II) methods of making urine collection systems, and (III) methods of using urine collection systems 10 are further described in the following additional embodiments.

Additional Embodiments

Urine Collection Systems

1. A urine collection system 100 comprising: a perforated sheet 10 having a perforated sheet outer periphery 11, a perforated sheet upper surface 12, a perforated sheet lower surface 13, and a plurality of perforated sheet apertures 14 (i) within the perforated sheet outer periphery 11, and (ii) extending from said perforated sheet upper surface 12 to said perforated sheet lower surface 13; wherein at least a portion of the perforated sheet apertures 14 within said plurality of perforated sheet apertures 14 comprises a urine backflow feature 15 that allows one-way urine flow through a given perforated sheet aperture 14, and prevents urine backflow through the given perforated sheet aperture 14.

2. The urine collection system 100 of embodiment 1, wherein said perforated sheet 10 has a perforated sheet length $L_S$ of up to about 8.0 feet (ft), a perforated sheet width $W_S$ of up to about 6.0 ft, and a perforated sheet thickness $T_S$ of up to about 2.0 centimeters (cm). It should be understood that perforated sheet 10 may have any desired dimensions.

3. The urine collection system 100 of embodiment 1 or 2, wherein said perforated sheet 10 has a perforated sheet length $L_S$ of from about 2.0 ft to about 4.0 ft, a perforated sheet width $W_S$ of from about 2.0 ft to about 4.0 ft, and a perforated sheet thickness $T_S$ of from about 1.0 cm to about 1.5 cm.

4. The urine collection system 100 of any one of embodiments 1 to 3, wherein said urine backflow feature 15 comprises an aperture shape 15' that prevents urine backflow.

Figure 1:
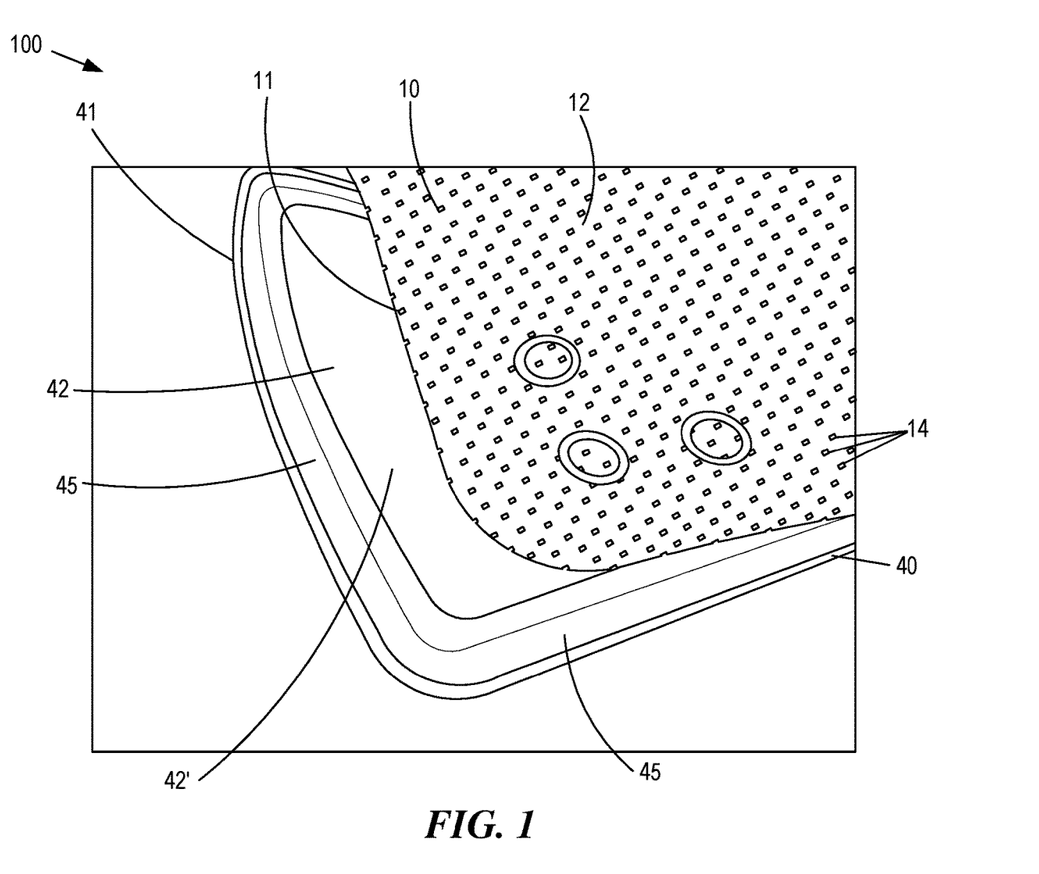
FIG. 1 is a perspective view of an exemplary urine collection system of the present invention.
Figure 2:
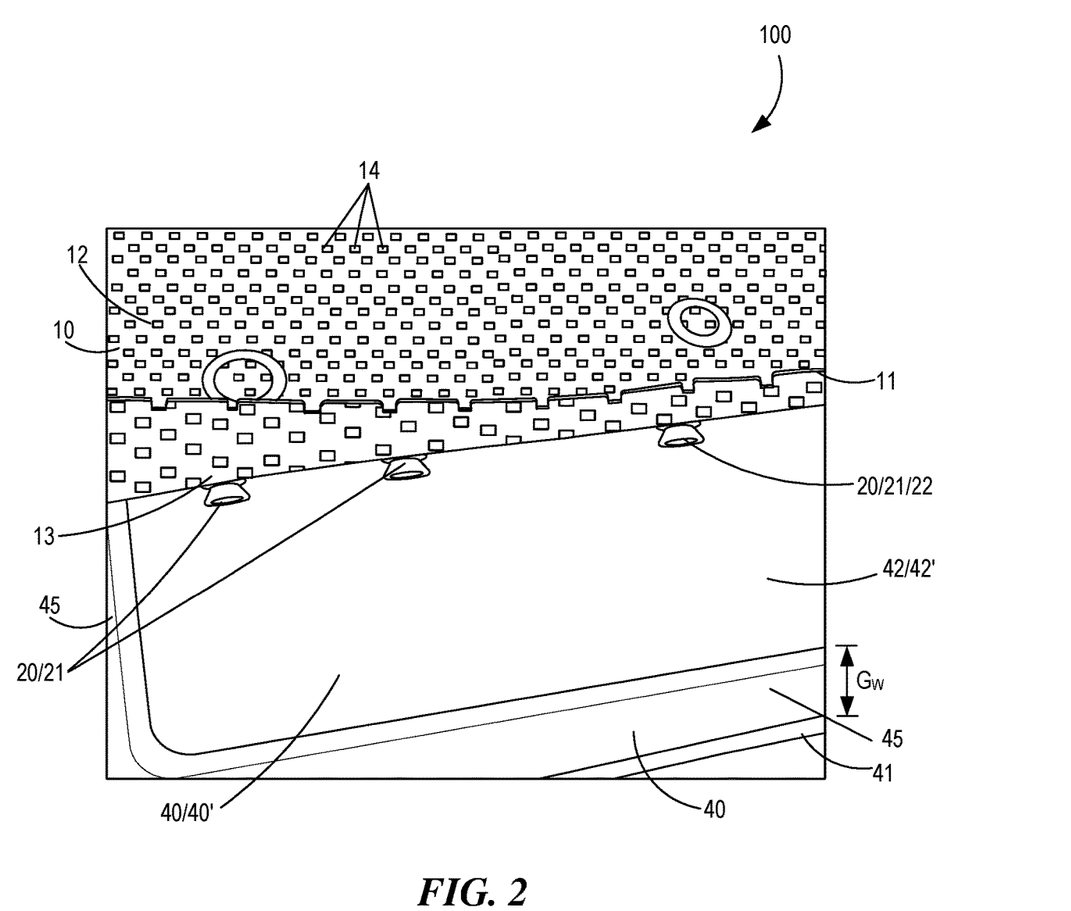
FIG. 2 is another perspective view of the exemplary urine collection system shown in FIG. 1 with a perforated sheet lower surface displayed.
Figure 3:
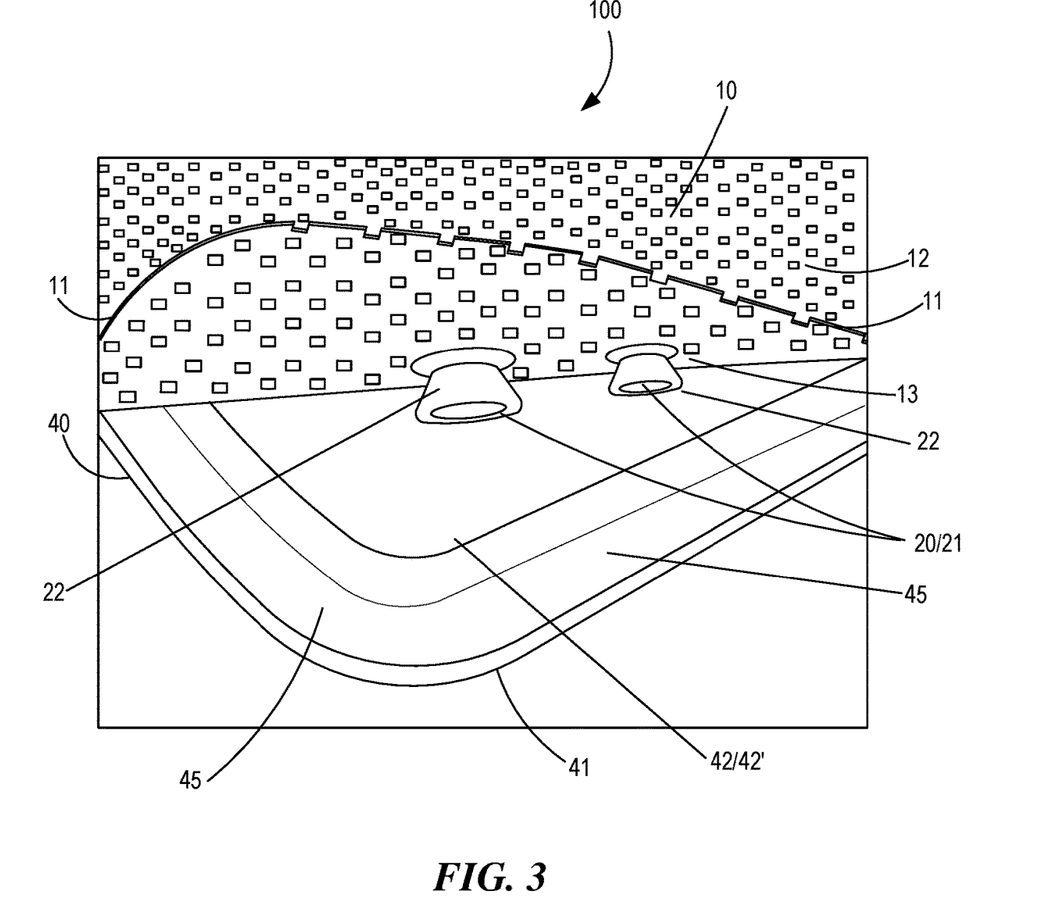
FIG. 3 is a close-up view of an exemplary perforated sheet lower surface of the exemplary urine collection system shown in FIG. 1.
Figure 4:
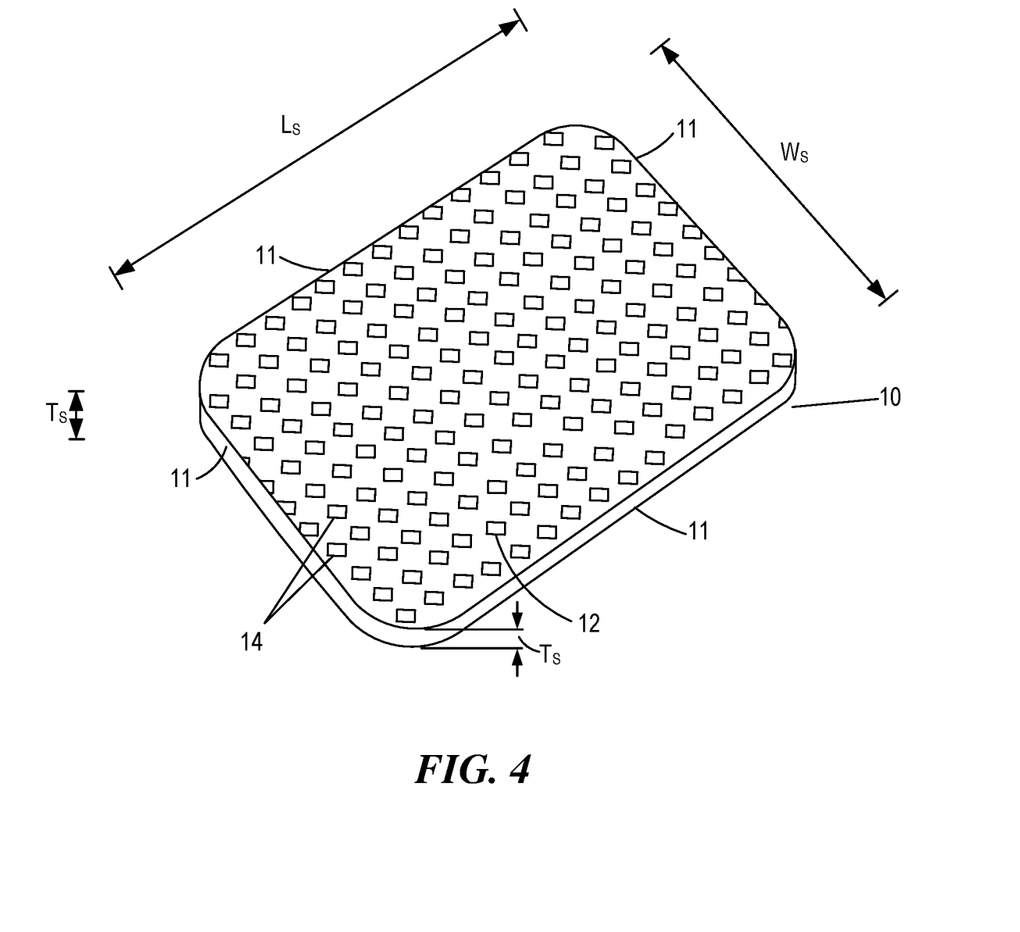
FIG. 4 is a perspective view of an exemplary perforated sheet suitable for use in the exemplary urine collection system shown in FIG. 1.
Figure 5:
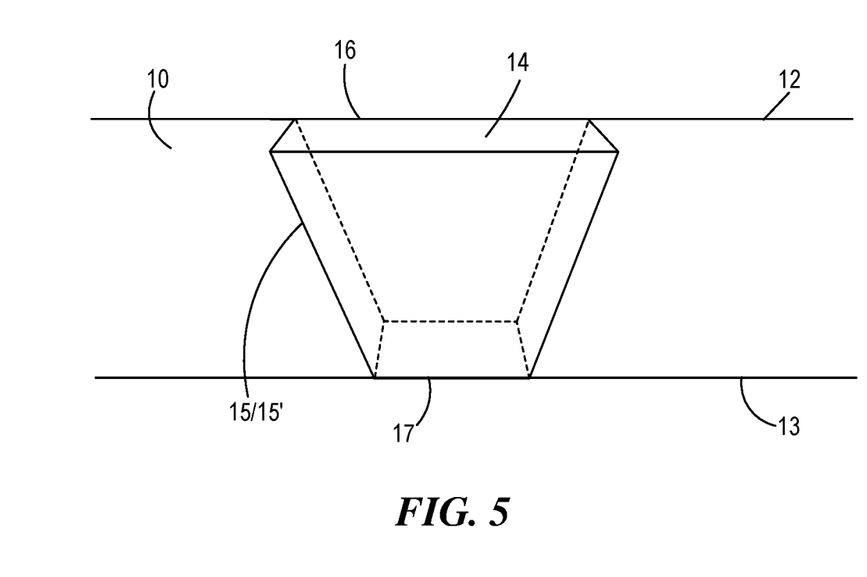
FIG. 5 is a side, cut-away view of an exemplary aperture shape suitable for use in the exemplary urine collection system shown in FIG. 1.

5. The urine collection system 100 of embodiment 4, wherein said aperture shape 15' comprises a cone shape 15' having a larger aperture inlet 16 along said perforated sheet upper surface 12 and a smaller aperture outlet 17 along said perforated sheet lower surface 13. See, for example, FIG. 5.

6. The urine collection system 100 of any one of embodiments 1 to 5, wherein said urine backflow feature 15 comprises one or more inner flow-controlling members 15" positioned within a given perforated sheet aperture 14. See, for example, FIG. 6.

Figure 6:
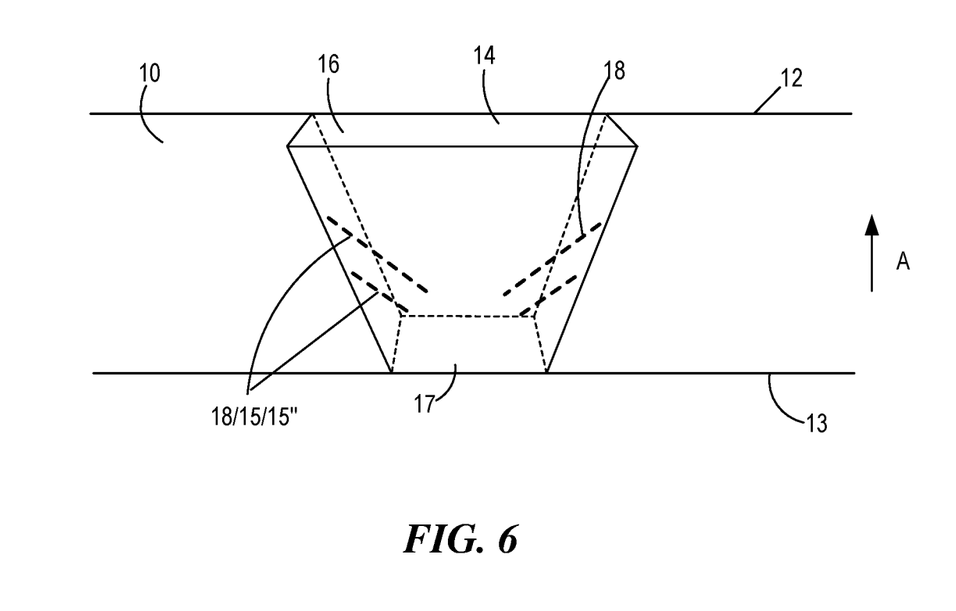
FIG. 6 is a side, cut-away view of an exemplary aperture with inner flow-controlling members therein, which is suitable for use in the exemplary urine collection system shown in FIG. 1.

7. The urine collection system 100 of embodiment 6, wherein said one or more inner flow-controlling members 15" comprise one or more aperture flaps 18 that move towards said perforated sheet upper surface 12 to close said given perforated sheet aperture 14 when exposed to urine backflow. As shown in FIG. 6, one or more aperture flaps 18 move in direction A depending on whether the one or more aperture flaps 18 are subjected to urine backflow pressure.

Figure 7:
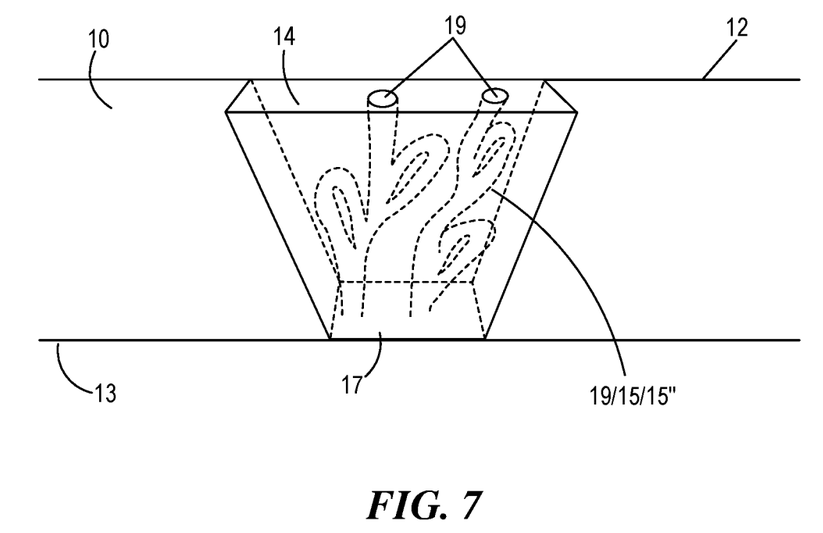
FIG. 7 is a side, cut-away view of an exemplary aperture with a Tesla valve (i.e., fluid flow) configuration, which is suitable for use in the exemplary urine collection system shown in FIG. 1.

8. The urine collection system 100 of embodiment 6, wherein said one or more inner flow-controlling members 15" comprise a Tesla valve configuration 19. See, for example, FIG. 7.

9. The urine collection system 100 of any one of embodiments 1 to 8, wherein said urine backflow feature 15 comprises one or more outlet flow-controlling members 15''' positioned along said perforated sheet lower surface 13 at an aperture outlet 17 of a given perforated sheet aperture 14.

Figure 8:
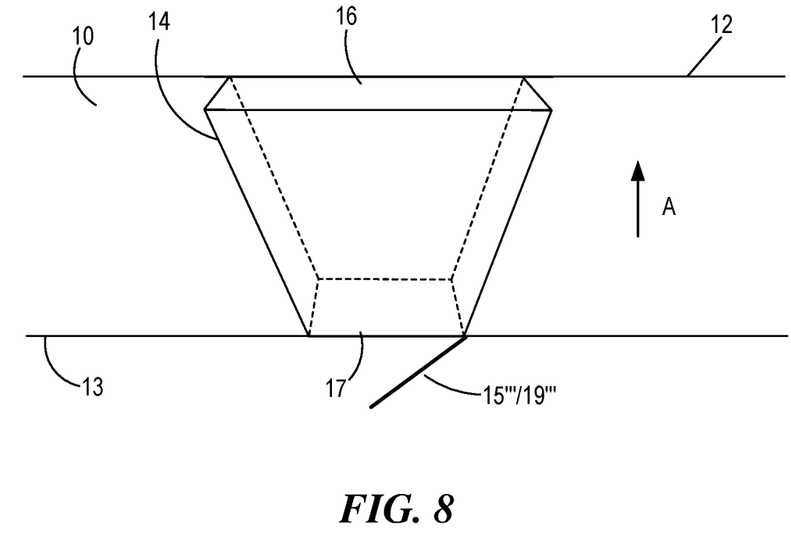
FIG. 8 is a side, cut-away view of an exemplary aperture with an outer flow-controlling member, which is suitable for use in the exemplary urine collection system shown in FIG. 1.
Figure 9:
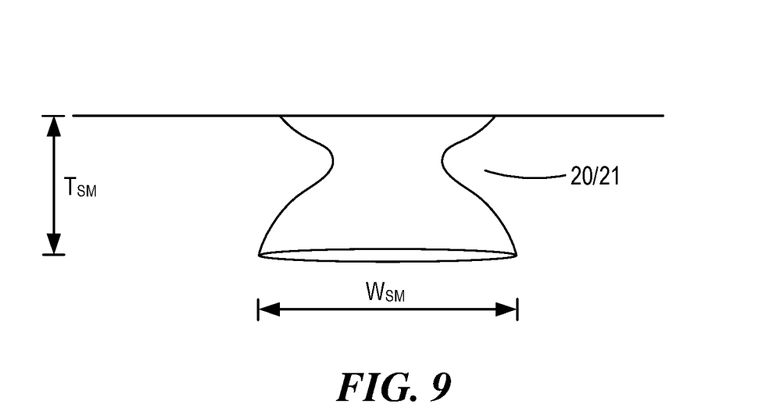
FIG. 9 is a side view of an exemplary suction cup suitable for use in the exemplary urine collection system shown in FIG. 1.

10. The urine collection system 100 of embodiment 9, wherein said one or more outlet flow-controlling members 15''' comprise one or more outlet flaps 19''' that move towards said perforated sheet upper surface 12 (i.e., in direction A) to close said given perforated sheet aperture 14 when exposed to urine backflow. See, for example, FIG. 8.

11. The urine collection system 100 of any one of embodiments 1 to 10, wherein all of the perforated sheet apertures 14 within said plurality of perforated sheet apertures 14 comprise said urine backflow feature 15.

12. The urine collection system 100 of any one of embodiments 1 to 11, wherein said plurality of perforated sheet apertures 14 comprises from about 20 to about 200 apertures 14 per square foot of said perforated sheet upper surface 12. It should be understood that perforated sheet 10 may have any number of perforated sheet apertures 14 per square foot of said perforated sheet upper surface 12.

13. The urine collection system 100 of any one of embodiments 1 to 12, wherein said plurality of perforated sheet apertures 14 comprises from about 100 to about 200 apertures 14 per square foot of said perforated sheet upper surface 12.

14. The urine collection system 100 of any one of embodiments 1 to 13, wherein said perforated sheet 10 comprises a non-absorbent, polymeric sheet 10. It should be understood that perforated sheet 10 may be formed from any type of polymer, and/or other elastomeric materials, either alone or in combination with one another and other possible materials such as synthetic (e.g., polymeric) or natural (e.g., cellulosic) fibers have any number of perforated sheet apertures 14 per square foot of said perforated sheet upper surface 12.

15. The urine collection system 100 of any one of embodiments 1 to 14, wherein said perforated sheet 10 comprises a non-absorbent, polypropylene sheet 10.

16. The urine collection system 100 of any one of embodiments 1 to 15, wherein said perforated sheet 10 further comprises a plurality of support members 20 extending from said perforated sheet lower surface 12, said plurality of support members 20 being capable of positioning said perforated sheet 10 above a flat surface 80 (e.g., a bed mattress top surface 81, a stretcher top surface (not shown), or a major surface portion 42' of a bottom sheet upper surface 42, discussed below). See, for example, FIGS. 2-3, 9, and 14.

17. The urine collection system 100 of embodiment 16, wherein said plurality of support members 20 comprise a plurality of suction cups 21. See again, for example, FIGS. 2-3, and 9.

18. The urine collection system 100 of embodiment 16 or 17, wherein said plurality of support members 20 comprises from about 16 to about 150 support members 20 per square foot of said perforated sheet lower surface 13. It should be understood that any number of support members 20 per square foot of said perforated sheet lower surface 13 may be used.

19. The urine collection system 100 of any one of embodiments 16 to 18, wherein said plurality of support members 20 comprises from about 36 to about 64 support members 20 per square foot of said perforated sheet lower surface 13. It should be understood that each support member 20 may have any desired size and dimensions. Typically, each support member 20 has an overall width $W_{SM}$ of from about 1.0 cm to about 4.0 cm, more typically, from about 1.0 cm to about 2.0 cm, and an overall thickness (i.e., height) $T_{SM}$ of from about 1.0 cm to about 4.0 cm, more typically, from about 1.0 cm to about 2.0 cm. See again, for example, FIG. 9.

20. The urine collection system 100 of any one of embodiments 16 to 19, wherein each support member 20 of said plurality of support members 20 comprises a non-absorbent, polymeric material 22. It should be understood that support members 20 may be formed from any type of polymer, and/or other elastomeric materials, either alone or in combination with one another and other possible materials such as synthetic (e.g., polymeric) or natural (e.g., cellulosic) fibers.

21. The urine collection system 100 of any one of embodiments 16 to 20, wherein each support member 20 of said plurality of support members 20 comprises polypropylene 22.

Figure 13:
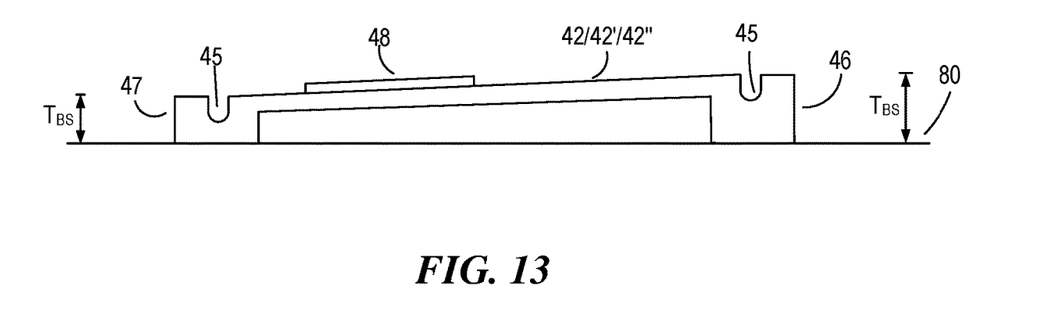
FIG. 13 is a possible cross-sectional view of the exemplary bottom sheet shown in FIG. 11 as viewed along line 13-13 shown in FIG. 12.
Figure 14:
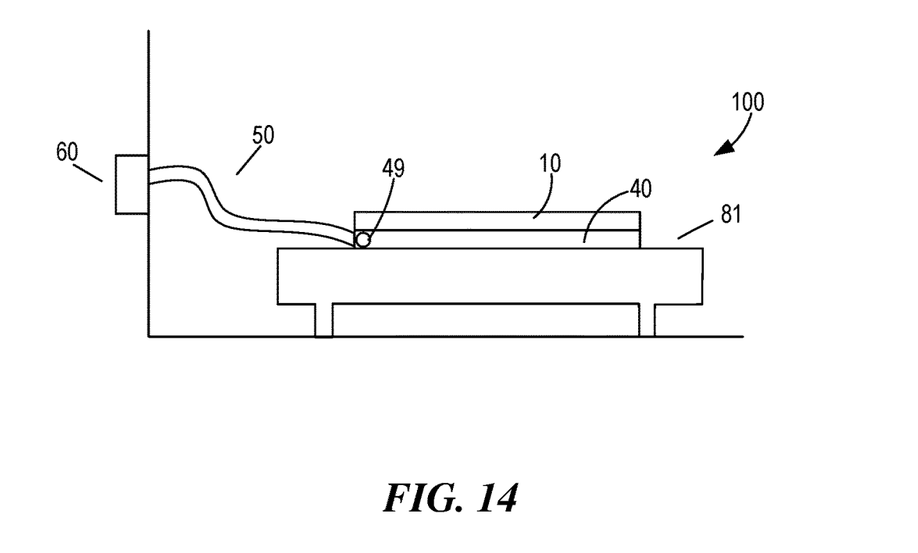
FIG. 14 is a side view of another exemplary urine collection system of the present invention, wherein the exemplary urine collection system comprises a perforated sheet as shown in FIG. 4 in combination with a bottom layer as shown in FIGS. 1-3 and 11-13, and a wall suction system.

22. The urine collection system 100 of any one of embodiments 16 to 21, wherein each support member 20 of said plurality of support members 20 is integrally connected to said perforated sheet lower surface 13.
23. The urine collection system 100 of any one of embodiments 1 to 22, further comprising: an absorbent layer 30 positioned below said perforated sheet 10, said absorbent layer 30 comprising a fiber-containing layer 31. See, for example, FIG. 10.
24. The urine collection system 100 of embodiment 23, wherein said absorbent layer 30 comprises synthetic fibers 32, natural fibers 32, superabsorbent particles 33, or any combination thereof.
25. The urine collection system 100 of embodiment 23 or 24, wherein said absorbent layer 30 covers more than 50% of said perforated sheet lower surface 13.
26. The urine collection system 100 of any one of embodiments 23 to 25, wherein said absorbent layer 30 has a basis weight of up to about 100 grams per square meter (gsm). It should be understood that absorbent layer 30 may have any desired basis weight of up to about 100 gsm or greater.
27. The urine collection system 100 of any one of embodiments 1 to 26, further comprising: a bottom sheet 40 positioned below said perforated sheet 10, said bottom sheet 40 having a bottom sheet upper surface 42, a bottom sheet lower surface 43, a major surface portion 42' extending within a plane P containing said bottom sheet upper surface 42, and one or more grooves 45 along a bottom sheet outer periphery 41 of said bottom sheet upper surface 42, wherein each groove 45 has a groove length $G_L$, a groove width $G_W$, and a groove depth $G_D$ that enables collection of urine along said bottom sheet outer periphery 41 of said bottom sheet upper surface 42. See, for example, FIGS. 11-12.
28. The urine collection system 100 of embodiment 27, wherein said one or more grooves 45 extend along at least 10% of a total length of said bottom sheet outer periphery 41. For example, bottom sheet 40 may comprise a single groove 45 extending along one side of bottom sheet 40 extending in a width direction.
29. The urine collection system 100 of embodiment 27 or 28, wherein said one or more grooves 45 extend along at least 50% of a total length of said bottom sheet outer periphery 41. For example, bottom sheet 40 may comprise grooves 45 extending along (i) one side of bottom sheet 40 extending in a width direction, and (i) one side of bottom sheet 40 extending in a length direction.
30. The urine collection system 100 of any one of embodiments 27 to 29, wherein said one or more grooves 45 extend along 100% a total length of said bottom sheet outer periphery 41. For example, bottom sheet 40 may comprise grooves 45 extending along all edges of the bottom sheet 40 similar to exemplary bottom sheet 40 shown in FIGS. 1-3, and 11-12.
31. The urine collection system 100 of any one of embodiments 27 to 30, wherein said groove length $G_L$ ranges from about 1.0 ft to about 8.0 ft, said groove width $G_W$ ranges from about 1.0 cm to about 5.0 cm, and said groove depth $G_D$ ranges from about 1.0 cm to about 3.0 cm.
32. The urine collection system 100 of any one of embodiments 27 to 31, wherein said bottom sheet 40 comprises a polymeric sheet 40'. It should be understood that bottom sheet 40 may be formed from any type of polymer, and/or other elastomeric materials, either alone or in combination with one another and other possible materials such as synthetic (e.g., polymeric) or natural (e.g., cellulosic) fibers.
33. The urine collection system 100 of any one of embodiments 27 to 32, wherein said bottom sheet 40 comprises a polypropylene sheet 40'.
34. The urine collection system 100 of any one of embodiments 27 to 33, wherein said bottom sheet 40 has a bottom sheet length $L_{BS}$ of up to about 8.0 ft, a bottom sheet width $W_{BS}$ of up to about 6.0 ft, and a bottom sheet thickness $T_{BS}$ of up to about 5.0 centimeters (cm). See again, FIGS. 11-12. Typically, bottom sheet 40 has (i) a bottom sheet length $L_{BS}$, and (ii) a bottom sheet width $W_{BS}$ that are similar to the perforated sheet length $L_S$ and the perforated sheet width $W_S$, respectively, of perforated sheet 10.
35. The urine collection system 100 of any one of embodiments 27 to 34, wherein said bottom sheet 40 has a bottom sheet length $L_{BS}$ of from about 2.0 ft to about 4.0 ft, a bottom sheet width $W_{BS}$ of from about 2.0 ft to about 4.0 ft, and a bottom sheet thickness $T_{BS}$ of from about 1.0 cm to about 1.5 cm.
36. The urine collection system 100 of any one of embodiments 27 to 35, wherein said plurality of support members 20 temporarily connect to said major surface portion 42' of said bottom sheet upper surface 42.
37. The urine collection system 100 of any one of embodiments 27 to 36, wherein said plurality of support members 20 temporarily connect to said major surface portion 42' of said bottom sheet upper surface 42, and comprise a plurality of suction cups 21.
38. The urine collection system 100 of any one of embodiments 34 to 37, wherein said bottom sheet 40 further comprises sheet structure that causes urine to flow from a head end 46 of said bottom sheet 40 towards a foot end 47 of said bottom sheet 40.
39. The urine collection system 100 of embodiment 38, wherein said sheet structure comprises an inclined surface 42" along said major surface portion 42' of said bottom sheet upper surface 42. See, for example, FIG. 13, which shows a possible cross-sectional view of bottom sheet 40 shown in FIG. 11, wherein head end 46 of said bottom sheet 40 is higher (i.e., $T_{BS}$ is greater at head end 46 than $T_{BS}$ at foot end 47 as shown in FIG. 13). It should be understood that in other embodiments, bottom sheet thickness $T_{BS}$ is substantially constant along bottom sheet 40.
40. The urine collection system 100 of embodiment 39, wherein said inclined surface 42" further comprises surface undulations 48 that guide urine towards said foot end 47 of said bottom sheet 40. See again, FIGS. 11-13.
41. The urine collection system 100 of any one of embodiments 27 to 40, wherein said bottom sheet 40 further comprises a urine outlet 49, said urine outlet 49 being connectable to a suction system, such as a wall suction system 60. See, for example, FIG. 14. It should be understood that other types of suction systems (not shown) may be used to remove urine from bottom sheet 40. For example, a portable suction system (not shown) that can be transported along with a patient (not shown) may be used with the urine collection system 100 of the present invention.
42. The urine collection system 100 of any one of embodiments 27 to 41, further comprising a length of tubing 50 capable of connecting said urine outlet 49 to a suction system, such as a wall suction system 60. See again, for example, FIG. 14.

43. The urine collection system 100 of any one of embodiments 1 to 42, further comprising a wall suction system 60.

44. The urine collection system 100 of any one of embodiments 1 to 42, further comprising a portable suction system (not shown).

Methods of Making Urine Collection Systems

45. A method of making the urine collection system 100 of any one of embodiments 1 to 44, said method comprising: forming the perforated sheet 10.

46. The method of embodiment 45, wherein said forming the perforated sheet 10 step comprises at least one of: thermoforming the perforated sheet 10 using one or more extruder surfaces, cutting the perforated sheet 10, thermoforming the perforated sheet 10 using one or more extruder surfaces, and punching the plurality of perforated sheet apertures 14 in the perforated sheet 10.

47. The method of embodiment 45 or 46, said method further comprising: forming the bottom sheet 40.

48. The method of embodiment 47, wherein said forming the bottom sheet 40 step comprises at least one of: thermoforming the bottom sheet 40 using one or more extruder surfaces, cutting the bottom sheet 40, and thermoforming the bottom sheet 40 using one or more mold surfaces.

49. The method of any one of embodiments 45 to 48, further comprising positioning the absorbent layer 30 below the perforated sheet 10.

50. The method of any one of embodiments 46 to 49, wherein said forming the perforated sheet 10 step comprises further comprising: forming the plurality of support members 20 extending from the perforated sheet lower surface 13.

51. The method of embodiment 50, wherein (i) said forming the perforated sheet 10 step, and (ii) said forming the plurality of support members 20 step occur simultaneously.

Methods of Using Urine Collection Systems

52. A method of collecting urine from a patient (not shown), said method comprising: positioning the perforated sheet 10 of any one of embodiments 1 to 44 under the patient.

53. The method of embodiment 52, further comprising: positioning the absorbent layer 30 between the perforated sheet 10 and the patient.

54. The method of embodiment 52 or 53, further comprising: positioning the bottom layer 40 between the perforated sheet 10 and the patient, and when present, below the absorbent layer 30.

55. The method of any one of embodiments 52 to 54, further comprising: attaching the urine collection system 100 to a suction system, such as a wall suction system 60.

56. The method of any one of embodiments 53 to 55, further comprising: replacing the absorbent layer 30 with a replacement absorbent layer 30.

57. The method of any one of embodiments 52 to 56, further comprising: replacing the perforated sheet 10 with a replacement perforated sheet 10.

58. The method of any one of embodiments 52 to 57, further comprising: measuring and monitoring a patient's urine output using the urine collection system 100. Such a step may be used to carefully monitor/manage fluid flow into and out of a given patient.

It should be understood that although the above-described urine collection systems, and methods are described as "comprising" one or more features, components or steps, the above-described urine collection systems, and methods may "comprise," "consists of," or "consist essentially of" any of the above-described features, components or steps of the urine collection systems, and methods. Consequently, where the present invention, or a portion thereof, has been described with an open-ended term such as "comprising," it should be readily understood that (unless otherwise stated) the description of the present invention, or the portion thereof, should also be interpreted to describe the present invention, or a portion thereof, using the terms "consisting essentially of" or "consisting of" or variations thereof as discussed below.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a urine collection system and/or method that "comprises" a list of elements (e.g., components or steps) is not necessarily limited to only those elements (or components or steps), but may include other elements (or components or steps) not expressly listed or inherent to the urine collection system and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a urine collection system and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Further, it should be understood that the herein-described urine collection systems, and/or methods may comprise, consist essentially of, or consist of any of the herein-described components, features, and steps, as shown in the figures with or without any feature(s) not shown in the figures. In other words, in some embodiments, the urine collection systems and/or methods of the present invention do not have any additional features other than those shown in the figures, and such additional features, not shown in the figures, are specifically excluded from the urine collection systems and/or methods. In other embodiments, the urine collection systems and/or methods of the present invention do have one or more additional features that are not shown in the figures.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Urine collection systems as described in embodiments 1 to 58 were prepared. The urine collection systems were used to collect urine from one or more patients in a hospital bed setting or nursing home bed setting.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A urine collection system comprising:
   (I) a perforated sheet having a perforated sheet outer periphery, a perforated sheet upper surface, a perforated sheet lower surface, and a plurality of perforated sheet apertures (i) within the perforated sheet outer periphery, and (ii) extending from said perforated sheet upper surface to said perforated sheet lower surface;
   wherein at least a portion of the perforated sheet apertures within said plurality of perforated sheet apertures comprises a urine backflow feature that allows one-way urine flow through a given perforated sheet aperture, and prevents urine backflow through the given perforated sheet aperture; and
   (II) a bottom sheet positioned below said perforated sheet, said bottom sheet having a bottom sheet upper surface, a bottom sheet lower surface, a major surface portion extending within a plane containing said bottom sheet upper surface, and one or more grooves along a bottom sheet outer periphery of said bottom sheet upper surface,
   wherein each groove has a groove length $G_L$, a groove width $G_W$, and a groove depth $G_D$ that enables collection of urine by said bottom sheet.

2. The urine collection system of claim 1, wherein said perforated sheet has a perforated sheet length $L_S$ of from about 2.0 ft to about 4.0 ft, a perforated sheet width $W_S$ of from about 2.0 ft to about 4.0 ft, and a perforated sheet thickness $T_S$ of from about 1.0 cm to about 1.5 cm.

3. The urine collection system of claim 1, wherein said urine backflow feature comprises an aperture shape that prevents urine backflow.

4. The urine collection system of claim 3, wherein said aperture shape comprises a cone shape having a larger aperture inlet along said perforated sheet upper surface and a smaller aperture outlet along said perforated sheet lower surface.

5. The urine collection system of claim 1, wherein said urine backflow feature comprises one or more inner flow-controlling members positioned within a given perforated sheet aperture, wherein said one or more inner flow-controlling members comprise one or more aperture flaps that move towards said perforated sheet upper surface to close said given perforated sheet aperture when exposed to urine backflow.

6. The urine collection system of claim 1, wherein said urine backflow feature comprises a Tesla valve configuration.

7. The urine collection system of claim 1, wherein said urine backflow feature comprises one or more outlet flow-controlling members positioned along said perforated sheet lower surface at an aperture outlet of a given perforated sheet aperture, wherein said one or more outlet flow-controlling members comprise one or more outlet flaps that move towards said perforated sheet upper surface to close said given perforated sheet aperture when exposed to urine backflow.

8. The urine collection system of claim 1, wherein all of the perforated sheet apertures within said plurality of perforated sheet apertures comprise said urine backflow feature.

9. The urine collection system of claim 1, wherein said perforated sheet further comprises a plurality of support members extending from said perforated sheet lower surface, said plurality of support members being capable of positioning said perforated sheet above a flat surface on which said plurality of support members contact.

10. The urine collection system of claim 9, wherein said plurality of support members comprise a plurality of suction cups.

11. The urine collection system of claim 1, wherein said one or more grooves extend along about 100% of a total length of said bottom sheet outer periphery.

12. The urine collection system of claim 1, wherein a plurality of support members of said perforated sheet temporarily connect to said major surface portion of said bottom sheet upper surface.

13. The urine collection system of claim 1, wherein said bottom sheet further comprises sheet structure that causes urine to flow relative to said bottom sheet.

14. The urine collection system of claim 13, wherein said sheet structure comprises an inclined surface along said major surface portion of said bottom sheet upper surface, wherein said inclined surface further comprises surface undulations that guide urine to flow in an intended direction relative to said bottom sheet.

15. The urine collection system of claim 1, wherein:
    said bottom sheet further comprises a urine outlet, said urine outlet being connectable to a suction system; and
    said surface undulations are adapted to guide urine along a path toward said urine outlet.

16. The urine collection system of claim 15, further comprising (i) a length of tubing capable of connecting said urine outlet to said suction system, and (ii) a suction system.

17. A method of collecting urine from a patient, said method comprising:
    positioning (I) the perforated sheet, and (II) the bottom sheet of claim 1 under the patient; and
    collecting urine from the patient.

18. The urine collection system of claim 1, wherein said urine collection system comprises a plurality of support members that extend from said perforated sheet lower surface and that are configured for temporarily connecting the perforated sheet lower surface to the bottom sheet upper surface.

19. The urine collection system of claim 18, where the plurality of support members comprises a plurality of suction cups.

20. The urine collection system of claim 18, wherein the plurality of support members comprises between about 16 to about 150 support members per square foot of the perforated sheet lower surface.

21. The urine collection system of claim 18, wherein the bottom sheet comprises a polymeric sheet.

22. The urine collection system of claim 1, wherein the groove length $G_L$, groove width $G_W$, and groove depth $G_D$ enable collection of urine along said bottom sheet outer periphery of said bottom sheet upper surface.

23. The urine collection system of claim 14, wherein the surface undulations are adapted to guide urine to flow toward a foot end of the bottom sheet.

\* \* \* \* \*